United States Patent
Goodwin et al.

(10) Patent No.: US 7,601,114 B2
(45) Date of Patent: *Oct. 13, 2009

(54) APPARATUS AND METHOD FOR ENHANCING TISSUE REPAIR IN MAMMALS

(75) Inventors: Thomas J. Goodwin, Kemah, TX (US); Clayton R. Parker, Safety Harbor, FL (US)

(73) Assignees: Regenetech, Inc., Sugar Land, TX (US); The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/563,934

(22) Filed: Nov. 28, 2006

(65) Prior Publication Data

US 2007/0100195 A1    May 3, 2007

Related U.S. Application Data

(62) Division of application No. 11/169,614, filed on Jun. 29, 2005, now Pat. No. 7,179,217.

(60) Provisional application No. 60/584,507, filed on Jun. 30, 2004.

(51) Int. Cl.
*A61N 2/00*    (2006.01)

(52) U.S. Cl. .................................................. 600/13
(58) Field of Classification Search .......... 600/9–15; 128/897–898; 607/2–3, 46
See application file for complete search history.

(56) References Cited

U.S. PATENT DOCUMENTS

| 4,993,413 | A | * | 2/1991 | McLeod et al. ............ 607/2 |
| 5,030,225 | A |   | 7/1991 | Aebischer et al. |
| 5,224,922 | A | * | 7/1993 | Kurtz ....................... 600/13 |
| 6,485,963 | B1 |  | 11/2002 | Wolf et al. |
| 2003/0158585 | A1 | | 8/2003 | Burnett |

* cited by examiner

*Primary Examiner*—Charles A Marmor, II
*Assistant Examiner*—Christine D Hopkins
(74) *Attorney, Agent, or Firm*—Ladas & Parry LLP

(57) ABSTRACT

An apparatus is introduced for the use of enhancing tissue repair in mammals. The apparatus includes a sleeve; an electrically conductive coil; a sleeve support; an electrical circuit configured to supply the coil with a square wave time varying electrical current sufficient to create approximately 0.05 gauss to 0.5 gauss. When in use, the sleeve of the apparatus is placed on a mammalian body part and the time varying electromagnetic force of from approximately 0.05 gauss to 0.5 gauss is generated on the mammalian body for an extended period of time so that the tissue is encouraged to be regenerated in the mammalian body part at a rate in excess of the normal tissue regeneration rate relative to regeneration without application of the time varying electromagnetic force

6 Claims, 2 Drawing Sheets

APPARATUS AND METHOD FOR ENHANCING TISSUE REPAIR IN MAMMALS

This is a Divisional Application, the parent application being Ser. No. 11/169, 614 filed on Jan. 29, 2005. The entire declaration, oath, specification, disclosure, and drawing figures from the parent application are hereby incorporated herein by reference, thereto.

FIELD OF THE INVENTION

The present invention relates to an apparatus for enhancing tissue repair in mammals. More particularly, the present invention relates to a sleeve in the form of an electromagnetic coil that fits over a mammalian body part. The present invention also relates to a method of using the apparatus.

BACKGROUND OF THE INVENTION

The power of the magnet is one of the most basic powers in nature. We know that magnetism itself was an ingredient in the primordial soup from which the universe and our planet came forth. Magnetism is the force that keeps order in the galaxy, allowing stars and planets to spin at significant velocities. An in a sense, our own planet's magnet field is responsible for protecting all life on earth.

Bio-magnetic therapy has long been the subject of controversy. Actually, bio-magnetic therapy is not new to everyone. Many veterinarians have been aware of bio-magnetic benefits for years, and use magnets to heal fractures quickly, thereby saving the lives of racehorses and other animals. Doctors treating professional athletes commonly recommend magnets to speed up recovery from painful injuries. And other physicians in a variety of specialties, including dermatologists, internists, pediatricians, and surgeons, have used magnets with varying claims of success.

The theory of magnetic healing can be seen by looking at early records of scientifically advanced civilizations, which tell us that magnetic forces have long been prized for their restorative properties. Ancient Greece discovered the very first natural magnet in the form of the lodestone, and Hippocrates, the father of medicine, noted its healing powers. The Egyptians, too, described the divine powers of the magnet in their writings, and Cleopatra frequently adorned herself with magnetic jewelry to preserve youthfulness. Chinese manuscripts dating back thousands of years describe the Eastern belief that the life force, termed "qi", is generated by the earth's magnetic field. Today, many believe that certain places on earth, such as Lourdes, France, and Sedona, Ariz., owe their healing powers to naturally high levels of this qi, or bio-magnetic energy.

Magnetic therapy is used in many countries such as Japan, China, India, Austria, and Germany. Although state-of-the-art American medicine uses techniques to monitor magnetic fields, such as electrocardiograms, electroencephalograms, and magnetic resonance imaging, it has not taken other forms of magnetic therapy seriously. More and more American studies, however, are considering whether or not magnetic therapy has medical value. As a result, increasing numbers of people are sleeping on magnetic beds at night and wearing small magnets during the day for greater energy, preventive purposes, and healing, many claiming varying degrees of success.

Research into magnet therapy is divided into two distinct areas: pulsed bioelectric magnet therapy and fixed magnetic therapy. Probably 85 to 90 percent of the scientific literature is on pulsed bioelectric bio-magnetic therapy; the remainder is on therapy with fixed solid magnets.

There are different schools of thought on the essential mechanisms of magnetic therapy, centered on questions of polarity, among other issues. However, fixed magnetic therapy has yet to be widely accepted by the scientific and medical community.

The effectiveness of using pulsed magnet fields to heal bone fractures and, to a lesser degree, soft tissue injures such as sprains and strains, has been debated for some time. Numerous scientific journals have reported these findings since the 1970s, and the FDA approves the use of pulsed electromagnetic fields for the treatment of nonunion bone fractures, which are fractures that will not heal on their own. It is believed that the pulsed electromagnetic fields penetrate the cast and get to the layer of skin that's moist and conductive. Then the electric field stops, but the magnetic field continues to do the healing work.

Numerous scientists have advanced theories for electromagnetic healing of many ailments, including osteoarthritis, rheumatoid arthritis, fibromyalgia, tension headaches, migraines, and Parkinson's disease.

All of the prior attempts to use electromagnetic therapy have used high levels of electromagnetism usually 50 gauss or more. While most of this therapy has used flat magnetic generators, a few have wrapped a magnetic blanket around a body member to attempt to regenerate or heal the body part. Some of the attempts have used pulsed waves, but such pulsed waves have been either on-off pulses or sinusoidal waves. No one, prior to this invention, has found the key to electromagnetic regeneration of mammalian tissue.

This invention has finally found the long sought after key to utilization of electromagnetic forces for tissue regeneration. To be successful in tissue regeneration, the electromagnetic force may be a square wave (Fourier curve) time varying electromagnetic wave at a level of from approximately 0.05 gauss to 0.5 gauss, a much lower level than previously contemplated by anyone.

SUMMARY OF THE INVENTION

The present invention relates to an apparatus for enhancing tissue repair in mammals comprising a sleeve for encircling a portion of a mammalian body part having an electrically conductive coil capable of generating an electromagnetic field when an electrical current is applied thereto, a means for supporting the sleeve on the mammalian body part, and a means for supplying the electrically conductive coil with a square wave time varying electrical current sufficient to create a time varying electromagnetic force of from approximately 0.05 gauss to 0.5 gauss within the interior of the coil in order that when the sleeve is placed on a mammalian body part and the time varying electromagnetic force of from approximately 0.05 gauss to 0.5 gauss is generated on the mammalian body part for an extended period of time, tissue regeneration within the mammalian body part is increased to a rate in excess of the normal tissue regeneration rate that would occur without application of the time varying electromagnetic force.

This invention also relates to a method of increasing tissue repair in a mammalian body part, said method comprising encompassing the mammalian body part with an apparatus for enhancing tissue repair having a sleeve for encircling a portion of a mammalian body part comprising an electrically conductive coil capable of generating an electromagnetic field when an electrical current is applied thereto, means for supporting the sleeve on the mammalian body part, and means for supplying the electrically conductive coil with a square wave time varying electrical current sufficient to create a time varying electromagnetic force of from approximately 0.05 gauss to 0.5 gauss within the interior of the coil; generating a time varying electromagnetic force of from approximately 0.05 gauss to 0.5 gauss on the mammalian body part by applying a time varying electrical current to the coil for a time period sufficient to enhance tissue regeneration within the body part at a rate in excess of the normal tissue regeneration rate that would occur without application of the time varying electromagnetic force.

DETAILED DESCRIPTION OF THE INVENTION

Figure 1:
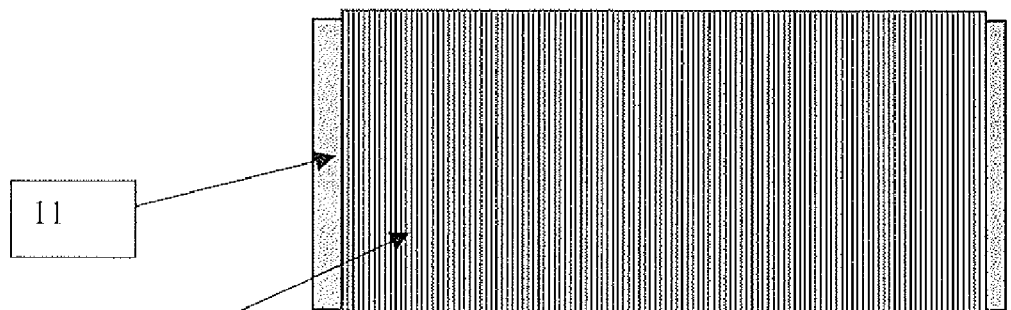
FIG. 1 is a side view of the sleeve of this invention showing the coil wound around the sleeve.
Figure 2:
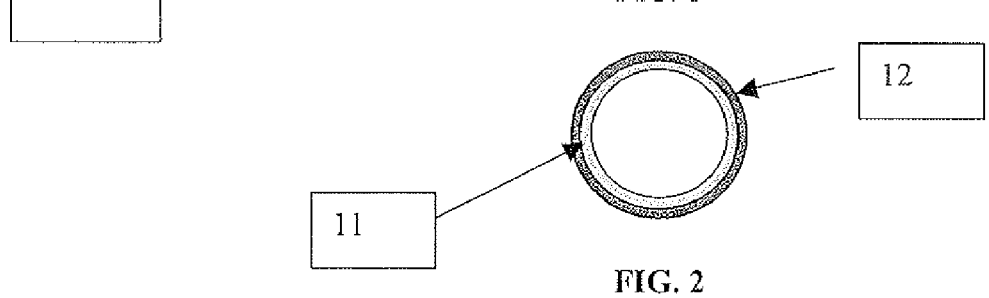
FIG. 2 is an end view of showing the coil on the sleeve.
Figure 3:
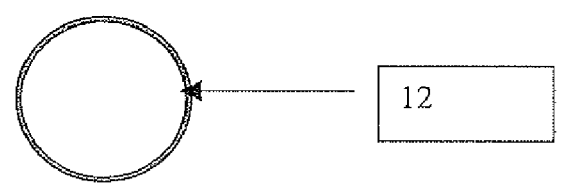
FIG. 3 is an end view of the coil.
Figure 4:
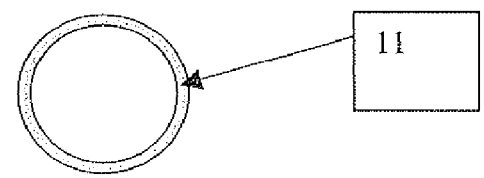
FIG. 4 is an end view of the sleeve.
Figure 5:
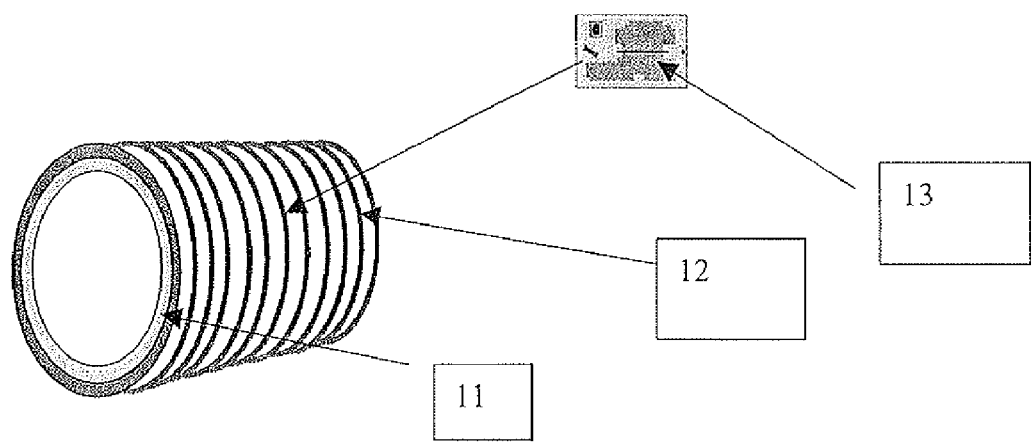
FIG. 5 is a perspective view of the sleeve with the coil and the time varying electrical current generator.
Figure 6:
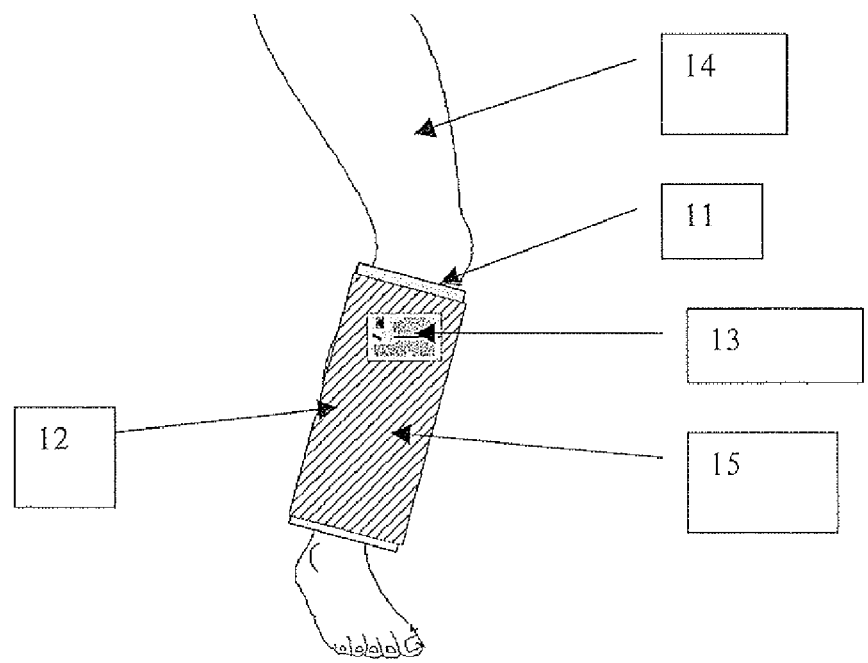
FIG. 6 is an illustration of the sleeve on a human leg.

This invention may be more fully described, but is not limited by the attached drawings and ensuing description in which, referring to the drawings, a sleeve portion 11 has a wire coil 12 wound around it. The sleeve portion is such that it fits over the mammalian body part to be treated. The wire coil is wound around the sleeve at approximately 10 windings per inch. A time varying electrical generator 13 is designed to be attached to the wire coil 12. The time varying electrical generator 13 is a standard part that can be purchased in stores supplying electrical products. It is powered by a standard 9-volt battery (not shown) and can be affixed to the sleeve by any means known in the art such as glue or Velcro (TM Velcro Industries B.V.). In use, the time varying electrical generator must be capable of generating a time varying electromagnetic force of 0.05 to 0.5 gauss within the sleeve. The sleeve is then placed on a mammalian body part such as human leg 14 to effect tissue regeneration thereof. The sleeve is kept on the body part for at least a week.

By way of example, if two groups of mammals having simple leg fractures are separated and one is given standard treatment and the other group has the time varying electromagnetic force applied to it with the sleeve of the apparatus of the present invention, those being treated with the time varying electromagnetic force will have substantially reduced healing times as compared to the group of mammals that were given standard treatment.

We claim:

1. A method of increasing tissue repair in a mammalian body part comprising:

encompassing the mammalian body part with an apparatus for enhancing tissue repair, said apparatus comprising a sleeve for encircling a portion of a mammalian body part, said sleeve comprising an electrically conductive coil capable of generating an electromagnetic field when an electrical current is applied thereto, means for supporting the sleeve on the mammalian body part; and means for supplying the electrically conductive coil with a square wave time varying electrical current sufficient to create a time varying electromagnetic force of from approximately 0.05 gauss to 0.5 gauss within the interior of the coil; and generating a time varying electromagnetic force of from approximately 0.05 gauss to 0.5 gauss on the mammalian body part by applying a time varying electrical current to the coil for a time period sufficient to enhance tissue regeneration within the body part at a rate in excess of the normal tissue regeneration rate that would occur without application of the time varying electromagnetic force.

2. A method of increasing tissue repair in a mammalian body part as in claim 1 wherein the coil is made of a ferromagnetic material.

3. A method of increasing tissue repair in a mammalian body part as in claim 1 wherein the coil is wound about the mammalian body part at about 10 windings per inch.

4. A method of increasing tissue repair in a mammalian body part as in claim 1 wherein the mammalian body part is a leg.

5. A method of increasing tissue repair in a mammalian body part as in claim 1 wherein the mammalian body part is an arm.

6. A method of increasing tissue repair in a mammalian body part as in claim 1 wherein the tissue being repaired is bone tissue.

* * * * *